United States Patent [19]

Takemoto

[11] Patent Number: 4,803,270
[45] Date of Patent: Feb. 7, 1989

[54] PROCESS OF PRODUCING FLUOROANILINE DERIVATIVES

[75] Inventor: Ichiki Takemoto, Toyonaka, Japan

[73] Assignee: Sumitomo Chemical Company, Limited, Osaka, Japan

[21] Appl. No.: 23,387

[22] Filed: Mar. 9, 1987

[30] Foreign Application Priority Data

| Mar. 10, 1986 [JP] | Japan | 61-52300 |
| Mar. 12, 1986 [JP] | Japan | 61-53921 |
| Nov. 14, 1986 [JP] | Japan | 61-272570 |
| Nov. 14, 1986 [JP] | Japan | 61-272571 |

[51] Int. Cl.⁴ .................. C07D 241/44; C07D 265/36
[52] U.S. Cl. .................... 544/105; 558/389; 558/394; 560/22; 562/437
[58] Field of Search ............ 544/52, 105, 354; 558/389, 394; 560/22; 562/437

[56] References Cited

U.S. PATENT DOCUMENTS

| 4,258,185 | 3/1981 | Nakao et al. | 544/114 |
| 4,619,687 | 10/1988 | Haga et al. | 544/105 X |
| 4,640,707 | 2/1987 | Nagano et al. | 544/105 X |
| 4,670,042 | 6/1987 | Haga et al. | 71/92 |
| 4,721,784 | 1/1988 | Combs | 544/105 |
| 4,729,784 | 3/1988 | Kume et al. | 544/105 Y |
| 4,734,124 | 3/1988 | Chang et al. | 544/105 X |

FOREIGN PATENT DOCUMENTS

| 0077938 | 5/1983 | European Pat. Off. |
| 0118982 | 9/1984 | European Pat. Off. |
| 16882 | 1/1984 | Japan. |

OTHER PUBLICATIONS

Chem. Abstracts, vol. 94, No. 7 (1981), 94:42637j.
Chem. Abstracts, vol. 90, No. 1 (1979), 90:6245p.
Chem. Abstracts, vol. 94, No. 17 (1981), 94:133973g.
Chem. Abstracts, vol. 101, No. 7 (1984), 101:55057h.
Chem. Abstracts, vol. 90, No. 22 (1979), 90:170149f.
Baliah et al., Indian Journal of Chemistry, vol. 10 (1972), pp. 917–918.

*Primary Examiner*—Richard L. Raymond
*Attorney, Agent, or Firm*—Birch, Stewart, Kolasch & Birch

[57] ABSTRACT

A process is disclosed for producing a fluoroaniline derivative of the formula:

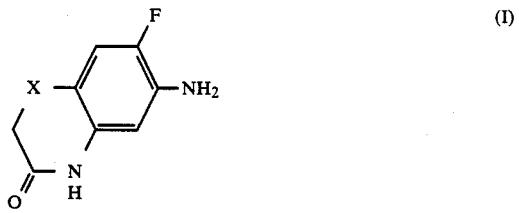

wherein X is an oxygen atom or an imino group. The process includes reacting 1,5-dichloro-2,4-dinitrobenzene with a glycol derivative of the formula:

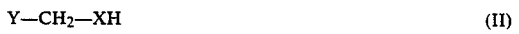

wherein X is defined above and Y is a cyano group, a carboxy group or a lower alkoxycarbonyl group to produce a chlorodinitrobenzene derivative of the formula:

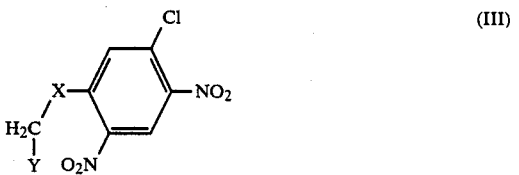

wherein X and Y are as defined above. The chlorodinitrobenzene derivative (III) is reacted with a metal fluoride to produce a fluorodinitrobenzene derivative of the formula:

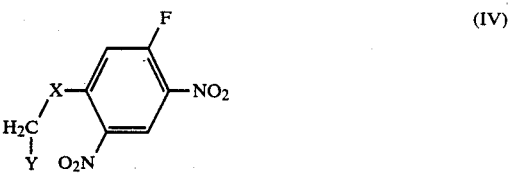

wherein X and Y are as defined above. The fluorodinitrobenzene derivative (IV) is subjected to reductive cyclization to obtain the fluoroaniline derivative (I).

37 Claims, No Drawings

PROCESS OF PRODUCING FLUOROANILINE DERIVATIVES

The present invention relates to fluoroaniline derivatives, and their production. More particularly, the invention relates to fluoroaniline derivatives of the formula:

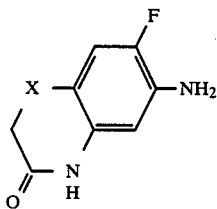
(I)

wherein X is an oxygen atom or an imino group useful as intermediates in the synthesis of argochemicals, and their production.

In the present application, the term "lower" is intended to mean any group having not more than 8 carbon atoms, preferably not more than 5 carbon atoms.

It is known that some tetrahydrophthalimide derivatives are useful as herbicides. For instance, 2-(7-fluoro-4-propargyl-2H-1,4-benzoxadin-3-(4H)-on-6-yl)-4,5,6,7-tetrahydroisoindole-1,3-dione is known to exert a strong herbicidal potency. However, this compound is usually produced from 2-nitro-5-fluorophenoxyacetic acid, which can be manufactured only through various steps with troublesome operations. Thus, the conventional process is not satisfactory from an industrial viewpoint.

In order to provide an advantageous process for the industrial production of tetrahydrophthalimide derivatives, an extensive study has been carried out and, as a result, it has now been found that the use of the fluoroaniline derivatives (I) as the intermediates can afford the objective tetrahydrophthalimide derivatives with great industrial advantages.

The fluoroaniline derivatives (I) according to the invention can easily be produced from the corresponding fluorodinitrobenzene derivatives (II) of the formula:

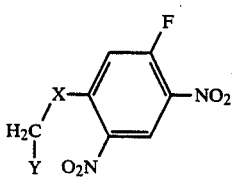
(II)

wherein Y is a cyano group, a carboxy group or a lower alkoxycarbonyl group and X is as defined above by the reductive cyclization, while they are readily converted into the objective tetrahydrophthalimide derivatives by introducing an appropriate substituent such as a propargyl group to the nitrogen atom at the 4-position as the functional group and reacting the resultant product with a tetrahydropthalic anhydride.

The process of this invention comprises subjecting the fluorodinitrobenzene derivative (II) to reductive cyclization to give the corresponding fluoroaniline derivative (I).

Examples of the fluorodinitrobenzene derivative (II) as the starting material in the process of the invention are 2,4-dinitro-5-fluorophenoxyacetic acid, methyl 2,4-dinitro-5-fluorophenoxyacetate, ethyl 2,4-dinitro-5-fluorophenoxyacetate, 2,4-dinitro-5-fluorophenoxyacetonitrile, N-(2,4-dinitro-5-fluorophenyl)glycine ethyl ester, N-(2,4-dinitro-5-fluorophenyl)aminoacetonitrile, etc.

The reductive cyclization may be achieved by any appropriate procedure such as catalytic reduction or chemical reduction.

The catalytic reduction may be effected in the presence of a catalyst such as platinum dioxide, palladium-carbon or Raney-nickel under a hydrogen atmosphere. The amount of the catalyst may be from catalytic to excessive, preferably from catalytic to 60% by weight, to the fluorodinitrobenzene derivative (II). It is normally carried out in an inert solvent such as an organic solvent (e.g. methanol, ethanol, isopropanol, ethyl acetate, tetrahydrofuran, toluene, xylene), water or their mixtures. The reaction is effected usually at a temperature of room temperature to 150° C. under an ordinary or elevated pressure for a period of 1 to 10 hours.

The chemical reduction is usually performed in the presence of iron powder and an acid. The amount of iron powder to be used may be not less than 5 mole, preferably from 6 to 10 mole, to one mole of the fluorodinitrobenzene derivative (II). As the acid, there may be employed an inorganic acid (e.g. hydrochloric acid, sulfuric acid), an organic acid (e.g. acetic acid), etc. It is usually carried out in an inert solvent, of which examples are water, an organic solvent (e.g. acetic acid, methanol, ethanol, isopropanol, tetrahydrofuran) and their mixtures. In general, the reaction is performed at a temperature of room temperature to 200° C., preferably of 80° to 150° C., under an ordinary pressure for a period of 1 to 20 hours.

Simultaneous with the reduction, the cyclization takes place to give the fluoroaniline derivative (I) in an excellent yield.

The fluorodinitrobenzene derivative (II) as the starting material in the process of the invention is novel and can be produced, for instance, by reacting 1,5-difluoro-2,4-dinitrobenzene with a glycol derivative of the formula:

wherein X and Y are each as defined above in an amount of 1 to 1.5 equivalents to the staring compound, usually in the presence of a basic catalyst in an inert solvent.

As the glycol derivative (III), there may be employed glycollic acid, lower alkyl glycolate (e.g. methyl glycolate, ethyl glycolate, propyl glycolate, butyl glycolate), glycine lower alkyl esters (e.g. glycine methyl ester, glycine ethyl ester, glycine n-butyl ester), glycolonitrile, aminoacetonitrile, etc. The amount of the glycol derivative (III) to be used is usually from 1 to 1.5 equivalents to the 1,5-difluoro-2,4-dinitrobenzene. Examples of the basic catalyst are sodium hydroxide, potassium hydroxide, potassium carbonate, sodium hydrogen carbonate, dipotassium hydrogen phosphate, tripotassium phosphate, pyridine, triethylamine, N,N-dimethylaniline, etc. The amount of the basic catalyst may be from a catalytic one to 4 equivalents, preferably from 1 to 3 equivalents, to the 1,5-difluoro-2,4-dinitrobenzene. Examples of the inert solvent are an organic solvent (e.g. toluene, xylene, acetone, tetrahydrofuran, ethyl acetate, methylene chloride, chloroform, chlorobenzene, acetonitrile, N,N-dimethylformamide, dimethylsulfoxide), water and their mixtures. In general, the reaction is carried out at a temperature of −50° to 200° C., preferably of −20° to 150° C., for a period of 1 to 10 hours.

The fluorodinitrobenzene derivative (II) also can be produced by reacting a chlorodinitrobenzene derivative of the formula:

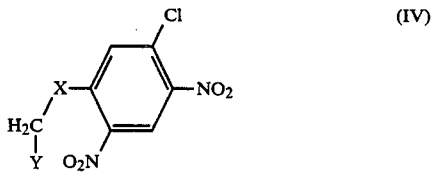

wherein X and Y are each as defined above with a metal fluoride, usually in an inert solvent.

As the metal fluoride, there may be used CsF, KF, NaF, CaF$_2$ or the like. Among them, KF is particularly preferred. The amount of the metal fluoride is usually from 1 to 5 equivalents, preferably from 1 to 3 equivalents, to the chlorodinitrobenzene derivative (IV). The presence of a phase transfer catalyst such as 18-crown-6 and TDA-1 in an amount of a catalytic one to 2 equivalents, preferably of 0.001 to 0.5 equivalents, to the chlorodinitrobenzene derivative (IV) in the reaction system is particularly favorable. Examples of the inert solvent are organic solvents (e.g. toluene, xylene, acetone, tetrahydrofuran, ethyl acetate, methylene chloride, chloroform, chlorobenzene, acetonitrile, N,N-dimethylformamide, dimethylsulfoxide) and their mixtures at a temperature of 0° to 200° C., preferably of 50° to 150° C., for a period of 1 to 10 hours.

Still, the chlorodinitrobenzene derivative (IV) may be prepared, for instance, by reacting 1,5-dichloro-2,4-dinitrobenzene with the glycol derivative (III), usually in the presence of a catalyst in an inert solvent. The glycol derivative (III) may be used in an amount of 1 to 5 equivalents, preferably of 1 to 2 equivalents, to the 1,5-dichloro-2,4-dinitrobenzene. As the catalyst, there is usually employed a basic one, of which examples are sodium hydroxide, potassium hydroxide, potassium carbonate, sodium hydrogen carbonate, dipotassium hydrogen phosphate, tripotassium phosphate, pyridine, triethylamine, N,N-dimethylaniline, etc. The amount of the basic catalyst is normally from a catalytic one to 5 equivalents, preferably from 1 to 2 equivalents to the 1,5-dichloro-2,4-dinitrobenzene. In addition to the basic catalyst, there may be used a copper catalyst (e.g. a cuprous chloride, cuprous oxide, copper powder) or a phase transfer catalyst (e.g. 18-crown-6, TDA-1). Examples of the inert solvent are organic solvents (e.g. toluene, xylene, acetone, tetrahydrofuran, ethyl acetate, methylene chloride, chloroform, chlorobenzene, acetonitrile, N,N-dimethylformamide, dimethylsulfoxide), water and their mixtures. The reaction is generally performed at a temperature of −50° to 200° C., preferably of −20° to 150° C., for a period of 1 to 30 hours.

As explained hereinabove, this invention can afford the fluoroaniline derivatives (I) in excellent yields. These fluoroaniline derivatives (I) can be readily converted into the corresponding tetrahydrophthalimide derivatives which are per se useful as agrochemicals. Thus, this invention provides an industrially advantageous process for production of the fluoroaniline derivatives (I) as well as the tetrahydrophthalimide derivatives.

The present invention will now be explained in further detail by the following Examples wherein % is by weight unless otherwise indicated.

EXAMPLE 1

Production of the chlorodinitrobenzene derivative (IV):

(1) A solution of 1,5-dichloro-2,4-dinitrobenzene (5.0 g), glycolonitrile (1.81 g) and anhydrous potassium carbonate (2.19 g) in dimethylformamide (20 g) was stirred at 25° to 30° C. for 24 hours. After completion of the reaction, the reaction mixture was diluted with water (200 ml) and extracted with ethyl acetate (200 ml). The organic layer was washed with water, dried over magnesium sulfate and concentrated. The precipitated crystals were collected by filtration and washed with ether to give crude crystals (4.16 g), which were recrystallized from methanol to give 2,4-dinitro-5-chlorophenoxyacetonitrile (3.18 g; yield, 58.5%). M.P., 117°–118° C.

Elementary analysis for $C_8H_4ClN_3O_5$: Calcd.: C, 37.30%; H, 1.57%; N, 16.31%; Cl, 13.77%. Found: C, 37.66%; H, 1.66%; N, 16.55%; Cl, 13.74%.

NMR δ (CDCl$_3$—DMSO—d$_6$): 5.40 (2H, s), 7.89 (1H, s), 8.20 (1H, s).

IR Nujol (cm$^{-1}$): 1580 (benzene ring); 1340 (nitro).

(2) In the same manner as above but using triethylamine (3.2 g) in place of anhydrous potassium carbonate, there was obtained 2,4-dinitro-5-chlorophenoxyacetonitrile (3.02 g; yield, 55.6%).

(3) A solution of 1,5-dichloro-2,4-dinitrobenzene (2.0 g), ethyl glycolate (1.32 g) and anhydrous potassium carbonate (0.88 g) and TDA-1 (0.27 g) in acetonitrile (10 g) was refluxed for 5 hours. After cooling, the reaction mixture was diluted with 3% hydrochloric acid (200 ml) and extracted with ethyl acetate. The organic layer was washed with 5% sodium carbonate solution, water and saturate sodium chloride solution in order, dried over magnesium sulfate, filtered and concentrated. The precipitated crystals were collected by filtration and recrystallized from methanol to give ethyl 2,4-dinitro-5-chlorophenoxyacetate (1.9 g; yield, 73.9%). M.P., 129°–130° C.

Elementary analysis for $C_{10}H_9ClN_2O_7$: Calcd.: C, 39.42%; H, 2.98%; N, 9.20%; Cl, 11.64%. Found: C, 39.27%; H, 2.99%; N, 9.15%; Cl, 11.54%.

NMR δ (CDCl$_3$—DMSO—d$_6$): 1.30 (3H, t, J=8 Hz), 4.28 (2H, q, J=8 Hz), 5.00 (2H, s), 7.40 (1H, s), 8.68 (1H, s).

IR Nujol (cm$^{-1}$): 1720 (ester); 1580 (benzene ring); 1340 (nitro).

EXAMPLE 2

Production of the fluorodinitrobenzene derivative (II):

(1) A suspension of 2,4-dinitro-5-chlorophenoxyacetonitrile (5.0 g) and potassium fluoride (1.7 g) in dimethylsulfoxide (25 g) was stirred at 83° to 85° C. for 1 hour. The reaction mixture was poured into ice-water (300 ml) and extracted with ethyl acetate. The organic layer was washed with water, dried over magnesium sulfate and concentrated. The precipitated crystals were collected by filtration and washed with ether to give crystalline 2,4-dinitro-5-fluorophenoxyacetonitrile (4.18 g; yield, 89.3%). M.P., 118°–118.5° C. (recrystallized from methanol).

Elementary analysis for $C_8H_4FN_3O_5$: Calcd.: C, 39.85%; H, 1.67%; N, 17.43%. Found: C, 39.72%; H, 1.83%; N, 17.38%.

NMR δ ($CDCl_3$—DMSO—$d_6$): 8.88 (1H, d, J=8 Hz), 7.84 (1H, d, J=13 Hz), 5.40 (2H, s).

IR Nujol ($cm^{-1}$): 1590 (benzene ring); 1350 (nitro).

(2) A solution of 2,4-dinitiro-5-chlorophenoxyacetonitrile (2.0 g), potassium fluoride (0.54 g) and 18-crown-6 (0.21 g) in acetonitrile (20 ml) was heated under reflux for 2 hours. The reaction mixture was poured into ice-water (200 ml) and extracted with ethyl acetate. Post-treatment in the same manner as above gave crystalline 2,4-dinitro-5-fluorophenoxyacetonitrile (1.7 g; yield, 90.8%).

(3) To a suspension of 1,5-difluoro-2,4-dinitrobenzene (2.0 g) and aminoacetonitrile sulfate (2.0 g) in acetone (40 g) kept below 8° C., a solution of sodium hydrogen carbonate (3.3 g) in water (50 g) was dropwise added, followed by stirring for 3.5 hours under ice-cooling. The reaction mixture was poured into ice-water and extracted with ethyl acetate. The organic layer was washed with water and concentrated to give N-(2,4-dinitro-5-fluorophenyl)aminoacetonitrile (2.0 g; yield, 87.5%). M.P., 166°–167° C. (recrystallized from methanol).

Elementary analysis for $C_8H_5FN_4O_4$: Calcd.: C, 40.01%; H, 2.10%; N, 23.33%. Found: C, 40.01%; H, 1.91%; N, 23.39%.

NMR δ ($CDCl_3$—DMSO—$d_6$): 9.10 (1H, d, J=8 Hz), 9.1 (1H, m), 7.19 (1H, d, J=14 Hz), 4.65 (2H, d, J=6 Hz).

IR Nujol ($cm^{-1}$): 3300 (NH), 1610 (benzene ring), 1570 (nitro).

(4) To a solution of 1,5-difluoro-2,4-dinitrobenzene (7.4 g) and triethylamine (4.4 g) in toluene (74 g) kept at room temperature, a mixture of glycolonitrile (3.1 g) and toluene (6.2 g) was dropwise added, followed by stirring at room temperature for 2 hours. The reaction mixture was poured into 5% hydrochloric acid and extracted with ethyl acetate. The organic layer was washed with water and concentrated to give 2,4-dinitro-5-fluorophenoxyacetonitrile (8.2 g; yield, 93.8%). M.P., 112°–113° C. (recrystallized from ethyl acetate-hexane).

NMR δ ($CDCl_3$—DMSO—$d_6$): 8.88 (1H, d, J=8 Hz), 7.84 (1H, d, J=13 Hz), 5.40 (2H, s).

IR Nujol ($cm^{-1}$): 1600 (benzene ring), 1510 and 1340 (nitro).

EI-MS m/z: 241 (M+), 186, 169, 97.

(5) To a suspension of 1,5-difluoro-2,4-dinitrobenzene (3.8 g) and anhydrous potassium carbonate (3.1 g) in acetonitrile (50 ml) kept at room temperature, a solution of glycolonitrile (1.5 g) in acetonitrile (10 ml) was dropwise added, followed by stirring at room temperature for 1 hour. The reaction mixture was heated and allowed to reflux for 30 minutes (inner temperature, 83° C.). After cooling, the resultant mixture was poured into water and extracted with ethyl acetate. The organic layer was washed with water and concentrated to give crystalline 2,4-dinitro-5-fluorophenoxyacetonitrile (4.0 g; yield, 89.1%).

(6) To a mixture of 1,5-difluoro-2,4-dinitrobenzene (2 g), acetone (20 g) and 50% aqueous glycolonitrile solution (1.2 g), a solution of sodium hydrogen carbonate (0.9 g) in water (18 g) was dropwise added at 27° to 30° C. in 5 minutes, and stirring was continued at 27° to 41° C. for 4.5 hours. After completion of the reaction, the reaction mixture was poured into 1% hydrochloric acid, extracted with ethyl acetate and concentrated. The precipitated crystals were collected by filtration and dried to give 2,4-dinitro-5-fluorophenoxyacetonitrile (2.0 g; yield, 83.0%).

(7) A suspension of ethyl 2,4-dinitro-5-chlorophenoxyacetate (2.0 g) and potassium fluoride (0.57 g) in dimethylsulfoxide (10 g) was stirred at a temperature of 90° to 101° C. After cooling, the reaction mixture was diluted with ice water (200 ml) and extracted with ethyl acetate. The organic layer was washed with water and saturated sodium chloride solution in order, dried over anhydrous magnesium sulfate and concentrated to give ethyl 2,4-dinitro-5-fluorophenoxyacetate (1.7 g; yield, 89.9%). M.P., 59.0°–59.5° C. (recrystallized from methanol).

Elementary analysis for $C_{10}H_9FN_2O_7$: Calcd.: C, 41.67%; H, 3.15%; N, 9.72%. Found: C, 41.51%; H, 3.08%; N, 9.61%.

NMR δ ($CDCl_3$—DMSO—$d_6$): 1.35 (3H, t, J=8 Hz), 4.32 (2H, q, J=8 Hz), 4.99 (2H, s), 7.10 (1H, d, J=12 Hz), 8.81 (1H, d, J=8 Hz).

IR Nujol ($cm^{-1}$): 1735 (ester), 1580 (benzene ring), 1330 (nitro).

EI-MS m/z: 288 (M+), 242, 214, 169.

(8) A suspension of ethyl 2,4-dinitro-5-chlorophenoxyacetate (2.0 g) and potassium fluoride (0.76 g) in N,N-dimethylformamide (10 g) was stirred at a temperature of 122° C. for 1.5 hours. After cooling, the reaction mixture was diluted with ice water (200 ml) and extracted with ethyl acetate. The organic layer was washed with water and saturated sodium chloride solution in order, dried over anhydrous magnesium sulfate and concentrated to give ethyl 2,4-dinitro-5-fluorophenoxyacetate (1.4 g; yield, 74.0%).

EXAMPLE 3

Production of the fluoroaniline derivative (I):

(1) A suspension of 2,4-dinitro-5-fluorophenoxyacetic acid (0.25 g) and platinum dioxide (80 mg) in ethanol (10 ml) was subjected to catalytic reduction at room temperature under an ordinary pressure until 130 ml of hydrogen was absorbed. The reaction mixture was filtered, and the filtrate was concentrated to give 7-fluoro-6-amino-2H-1,4-benzoxazin-3(4H)-one (0.16 g; yield, 91.4%). M.P., more than 300° C.

NMR δ ($CDCl_3$—DMSO—$d_6$): 10.25 (1H), 6.70 (1H, d, J=12 Hz), 6.53 (1H, d, J=9 Hz), 4.50 (2H, s), 4.00 (2H).

IR Nujol ($cm^{-1}$): 3350 (NH), 1690 (CONH).

EI-MS m/z: 182 (M+), 113.

(2) A suspension of 2,4-dinitro-5-fluorophenoxyacetic acid (2.0 g) and 10% palladium-carbon (hydrated) (1.0 g) in ethanol (30 ml) was subjected to catalytic reduction at room temperature under an ordinary pressure until 1000 ml of hydrogen was absorbed. The reaction mixture was filtered, and the filtrate was concentrated to give 7-fluoro-6-amino-2H-1,4-benzoxazin-3(4H)-one (1.3 g; yield, 92.8%).

(3) Iron powder (5.6 g) was suspended in 5% acetic acid (112 g), and a solution of 2,4-dinitro-5-fluorophenoxyacetonitrile (2.4 g) in acetic acid (48 g) was dropwise added thereto under reflux, followed by refluxing for an additional 1 hour. The reaction mixture was filtered, and the filtrate was extracted with ethyl acetate. The extract was concentrated, and the precipitated crystals were collected by filtration and washed with a mixture of hexane and ether to give 7-fluoro-6- amino-2H-1,4-benzoxazin-3-(4H)-one (1.3 g; yield, 71.7%).

(4) A suspension of 2,4-dinitro-5-fluorophenyl)glycine ethyl ester (2.0 g) and 10% palladium-carbon (hydrated) (1.0 g) in ethanol (30 ml) was subjected to catalytic reduction at room temperature under an ordinary pressure until 1000 ml of hydrogen was absorbed. The reaction mixture was filtered, and the filtrate was concentrated to give 6-fluoro-7-amino-1,2-dihydroquinoxalin-2-one (1.24 g; yield, 99.4%). M.P., more than 300° C.

NMR δ (CDCl$_3$—DMSO—d$_6$): 10.00 (1H), 6.30 (1H), 6.42 (1H, d, J=12 Hz), 6.39 (1H, d, J=8 Hz), 4.02 (2H), 3.62 (2H, s).

IR Nujol (cm$^{-1}$): 3455 (NH), 1680 (CONH).

EI-MS m/z: 181 (M+), 179, 151, 97.

(5) A suspension of ethyl 2,4-dinitro-5-fluorophenoxyacetate (1.3 g) and 5% palladium-carbon (0.35 g) in ethanol (30 ml) was subjected to catalytic reduction at room temperature under an ordinary pressure until 600 ml of hydrogen was absorbed. The reaction mixture was filtered, and the filtrate was concentrated to give 7-fluoro-6-amino-2H-1,4-benzoxazin-3(4H)-one (0.68 g; yield, 82.8%).

(6) N-(2,4-Dinitro-5-fluorophenyl)glycine ethyl ester (9.32 g), 2% palladium-carbon (50% hydrated) (10 g) and ethanol (200 ml) were charged into an autoclave, and catalytic reduction was carried out at room temperature under an initial pressure of 37 atm. After the reaction was completed, the reaction mixture was filtered, and the filtrate was concentrated to give 6-fluoro-7-amino-1,2-dihydroquinoxalin-2-one (4.0 g; yield, 68.0%).

What is claimed is:

1. A process for producing a fluoroaniline derivative of the formula:

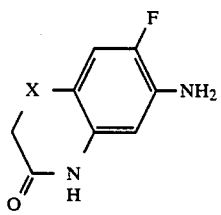

(I)

wherein X is an oxygen atom or an imino group, which comprises (a) reacting 1,5-dichloro-2,4-dinitrobenzene with a glycol derivative of the formula:

Y—CH$_2$—XH  (II)

wherein X is as defined above and Y is a cyano group, a carboxy group or a lower alkoxycarbonyl group to produce a chlorodinitrobenzene derivative of the formula:

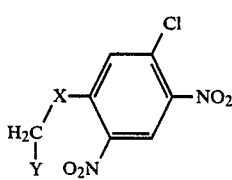

(III)

wherein X and Y are each as defined above, (b) reacting the chlorodinitrobenzene derivative (III) with a metal fluoride to produce a fluorodinitrobenzene derivative of the formula:

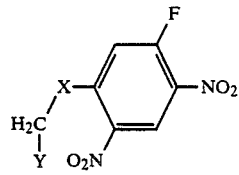

(IV)

wherein X and Y are each as defined above and (c) subjecting the fluorodinitrobenzene derivative (IV) to reductive cyclization.

2. A process for producing a fluoroaniline derivative of the formula:

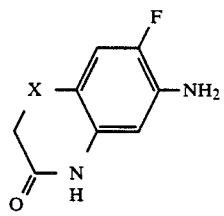

(I)

wherein X is an oxygen atom or an imino group, which comprises (a) reacting 1,5-difluoro-2,4-dinitrobenzene with a glycol derivative of the formula:

Y—CH$_2$—XH wherein X is as defined above and Y is a cyano group, a carboxy group or a lower alkoxycarbonyl group to produce a fluorodinitrobenzene derivative of the formula:

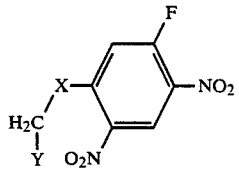

wherein X and Y are each as defined above and (b) subjecting the fluorodinitrobenzene derivative to reductive cyclization.

3. The process according to claim 1, wherein step (c) is carried out in the presence of a catalyst under a hydrogen atmosphere.

4. The process according to claim 3, wherein the catalyst is platinum dioxide, palladium-carbon or Raney-nickel.

5. The process according to claim 1, wherein step (c) is carried out by chemical reduction.

6. The process according to claim 5, wherein the chemical reduction is performed in the presence of metal and an acid.

7. The process according to claim 6, wherein the metal is iron powder or zinc powder.

8. The process according to claim 6, wherein the acid is hydrochloric acid, sulfuric acid or acetic acid.

9. The process according to claim 1, wherein the glycol derivative (II) in step (a) is glycolonitrile, aminoacetonitrile, lower alkyl glycolate or glycine lower alkyl ester.

10. The process according to claim 1, wherein the molar ratio of 1,5-dichloro-2,4-dinitrobenzene and the glycol derivative in step (a) is 1:1–1.5.

11. The process according to claim 1, wherein step (a) is carried out in the presence of a basic catalyst.

12. The process according to claim 11, wherein the basic catalyst is an inorganic base.

13. The process according to claim 12, wherein inorganic base is sodium hydroxide, potassium hydroxide, potassium carbonate or sodium hydrogen carbonate.

14. The process according to claim 11, wherein the basic catalyst is an organic amine.

15. The process according to claim 14, wherein the organic amine is pyridine, triethylamine or N,N-dimethylaniline.

16. The process according to claim 11, wherein the basic catalyst is used in an amount of 1 to 2 equivalents to one equivalent of 1,5-dichloro-2,4-dinitrobenzene.

17. The process according to claim 1, wherein step (a) is effected at a temperature of −20° to 150° C.

18. The process according to claim 1, wherein the metal fluoride in step (b) is alkali metal fluoride or alkaline earth metal fluoride.

19. The process according to claim 18, wherein the alkali metal fluoride is potassium fluoride.

20. The process according to claim 1, wherein the metal fluoride in step (b) is used in an amount of 1 to 5 equivalents to one equivalent of the chloronitrobenzene derivative.

21. The process according to claim 1, wherein step (b) is carried out in the presence of a phase transfer catalyst.

22. The process according to claim 21, wherein the phase transfer catalyst is used in an amount of 0.001 to 0.5 equivalents to one equivalent of the chlorodinitrobenzene derivative.

23. The process according to claim 2, wherein the glycol derivative is glycolonitrile, aminoacetonitrile, lower alkyl glycolate or glycine lower alkyl ester.

24. The process according to claim 2, wherein the molar ratio of 1,5-dichloro-2,4-dinitrobenzene and the glycol derivative in step (a) is 1:1–5.

25. The process according to claim 2, wherein the reaction in step (a) is carried out in the presence of a basic catalyst.

26. The process according to claim 25, wherein the basic catalyst is an inorganic base.

27. The process according to claim 26, wherein inorganic base is sodium hydroxide, potassium hydroxide, potassium carbonate or sodium hydrogen carbonate.

28. The process according to claim 25, wherein the basic catalyst is an organic amine.

29. The process according to claim 28, wherein the organic amine is pyridine, triethylamine or N,N-dimethylaniline.

30. The process according to claim 25, wherein the the basic catalyst is used in an amount of 1 to 2 equivalents to one equivalent of 1,5-dichloro-2,4-dinitrobenzene.

31. The process according to claim 2, wherein step (a) is carried out at a temperature of −20° to 150° C.

32. The process according to claim 2, wherein step (b) is carried out in the presence of a catalyst under a hydrogen atmosphere.

33. The process according to claim 32, wherein the catalyst is platinum dioxide, palladium carbon or Raney nickel.

34. The process according to claim 2, wherein step (b) is carried out by chemical reduction.

35. The process according to claim 34, wherein the chemical reduction is performed in the presence of metal and an acid.

36. The process according to claim 35, wherein the metal is iron powder or zinc powder.

37. The process according to claim 35, wherein the acid is hydrochloric acid, sulfuric acid or acetic acid.

* * * * *